United States Patent [19]
DiNitto et al.

[11] Patent Number: 4,466,878
[45] Date of Patent: Aug. 21, 1984

[54] ELECTROCHEMICAL ELECTRODE ASSEMBLY

[75] Inventors: Robert G. DiNitto, Acton; John C. Harris, Andover; Robert F. Maciel, Tyngsboro, all of Mass.

[73] Assignee: Instrumentation Laboratory Inc., Lexington, Mass.

[21] Appl. No.: 457,509

[22] Filed: Jan. 12, 1983

[51] Int. Cl.³ .............................................. G01N 27/54
[52] U.S. Cl. .................................... 204/415; 204/1 T; 128/635
[58] Field of Search .................. 204/297 R, 415, 416, 204/417, 418, 419, 420, 1 P, 286; 128/635

[56] References Cited

U.S. PATENT DOCUMENTS

| | | | |
|---|---|---|---|
| 3,351,544 | 11/1967 | Medlar | 204/195 |
| 3,476,672 | 11/1969 | Synder et al. | 204/420 |
| 3,649,505 | 3/1972 | Strickler et al. | 204/195 |
| 3,718,567 | 2/1973 | Haddad et al. | 204/195 |
| 3,875,037 | 1/1975 | Krull et al. | 204/415 |
| 4,176,032 | 11/1979 | Stevenson, Jr. | 204/415 |
| 4,233,143 | 11/1980 | Knudsen | 204/415 |
| 4,273,638 | 6/1981 | Swartz | 204/415 |
| 4,285,791 | 8/1981 | Schmidt-Rabenau | 204/416 |
| 4,303,076 | 12/1981 | Danek | 128/635 |

Primary Examiner—R. L. Andrews
Assistant Examiner—Terryence Chapman

[57] ABSTRACT

A replaceable cartridge assembly for use with electrochemical analysis apparatus includes a housing of electrically insulating material that defines an annular electrolyte chamber with coupling structure at one end of the housing and a chamber port at the other end of the housing. A selectively permeable membrane extends across the port in sealing relation thereto. An elongated guide channel within the housing is surrounded by the electrolyte chamber and receives a cooperating connector stem that carries a socket-temperature sensor assembly. A cathode electrode projects coaxially upwardly from the end wall of the guide channel into the stem socket and the lower portion of the cathode electrode extends through the guide channel end wall such that its tip is exposed to the membrane. An anode electrode is disposed in the electrolyte chamber with an external contact surface adjacent the coupling structure. Electrolyte in the annular chamber extends through the chamber port into the region between the membrane and the tip of the cathode electrode to provide an electrically conductive path between the anode and cathode electrodes.

20 Claims, 8 Drawing Figures

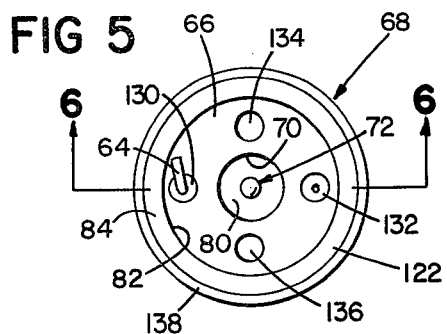
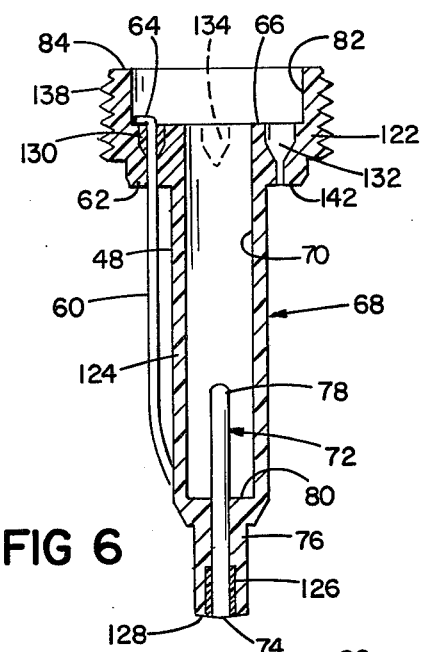
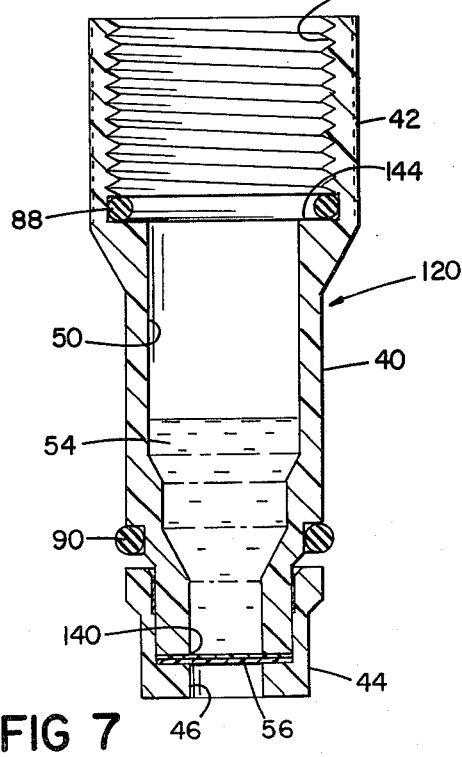
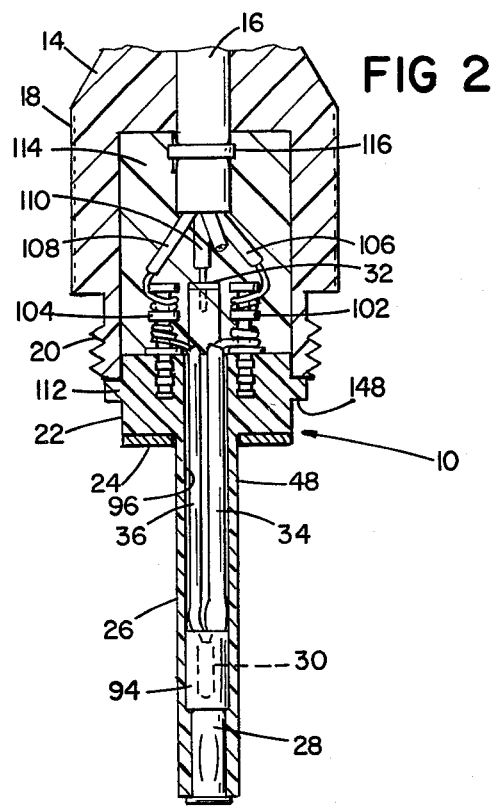
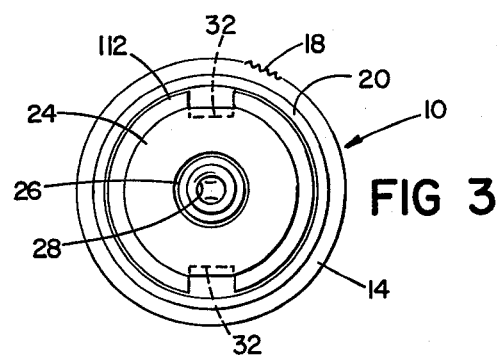
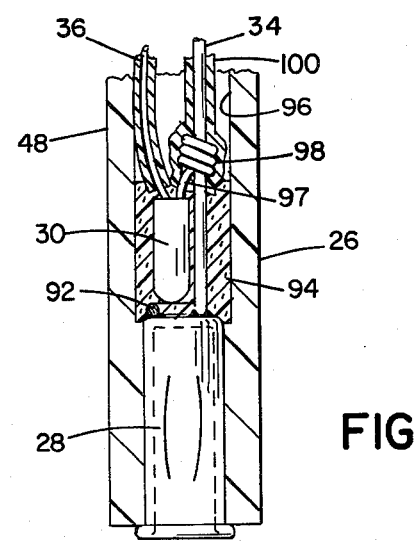

ELECTROCHEMICAL ELECTRODE ASSEMBLY

This invention relates to electrochemical electrode analysis systems and more particularly to electrode assemblies of the type that employ a membrane interposed between an electrode and the sample to be analyzed.

Such electrode assemblies are useful for sensing a variety of substaces including gases such as oxygen and carbon dioxide, in which the direct measurement of the gas is made potentiometrically. In the case of oxygen, for example, when the electrode assembly is exposed to a fluid containing oxygen, the oxygen that diffuses across the permeable membrane in response to a partial pressure difference participates in an electrochemical reaction and affects an electric current flow between polarized electrodes, the current varying as a function of the partial pressure of the oxygen and therefore providing an indication of its concentration.

Electrode assemblies of this type require frequent maintenance due, for example, to membrane deterioration or to electrolyte depletion. Care must be taken in handling electrolyte and in guarding against damage to exposed portions of the electrode assembly. A critical aspect frequently is the relationship between a permeable membrane that is spaced from an immediately adjacent electrode by a thin film of electrolyte, and in many electrode constructions, it has been difficult to change or replace the membrane properly. While a number of arrangements have been proposed to facilitate and simplify membrane replacement, none have been completely satisfactory. Another aspect is the thermal sensitivity of electrode systems of this type, a differential in temperature between the reaction site (at the tip of the cathode adjacent the membrane) and the assumed measurement temperature producing a significant error.

In accordance with one aspect of the invention there is provided a replaceable cartridge assembly for use with electrochemical analysis apparatus, the cartridge assembly including a housing of electrically insulating material that defines an annular electrolyte chamber with coupling structure at one end of the housing and a chamber port at the other end of the housing. A selectively permeable membrane extends across the port in sealing relation thereto. An elongated guide channel within the housing is surrounded by the electrolyte chamber and a cathode electrode contact surface is at the base of the guide channel with the cathode electrode extending through the guide channel end wall such that its tip is exposed at the end surface of the housing. An anode electrode has a contact surface adjacent the coupling structure with a major portion of the anode electrode disposed in the electrolyte chamber. Electrolyte in the annular chamber is disposed annularly around the cathode electrode and extends through the chamber port into the region between the membrane and the tip of the cathode electrode to provide an electrically conductive path between the anode and cathode electrodes.

In accordance with another aspect of the invention there is provided an electrochemical electrode assembly that includes a detachable cartridge component and a cooperating connector component that includes an elongated projecting stem with a temperature sensor-electrical socket assembly in the end of the stem and an anode contact adjacent the end of the stem remote from the socket. As the cartridge is being attached to the connector component, a projecting portion of the cathode electrode pilots the stem socket and then the end of the anode electrode electrically engages the anode contact. The temperature sensor is located within the electrode assembly close to the reaction site at the cathode tip. In preferred embodiments, thermal isolation of the temperature sensor is enhanced by thermal insulation (a sealed air chamber in a particular embodiment) in the stem between the sensor and the connector body and by an annular air gap between the connector stem and the cartridge body.

In a particular embodiment, both the cathode electrode and the anode electrode are lengths of silver wires, and are arranged such that no solder or other material that might produce an extraneous half-cell potential is used in the cartridge. The cartridge is easy to manufacture, a screw thread arrangement facilitating assembly with the desired precision of membrane and cathode relationship, as well as ready attachment and detachment of the cartridge component from the connector component. Contact engagement in that embodiment is made with helical, wiping action, and both contact portions are protectively recessed within the cartridge. In the electrode assembly, the thermally shielded temperature sensor is located close to the reaction site, is embedded in thermal unity with a resilient contact socket at the end of a cylindrical tubular stem that has a length to diameter ratio of more than four, and is further thermally shielded by the annular air gap between the stem and the cartridge cavity in which it is received. That compact electrochemical electode assembly of a replaceable cartridge unit (that includes anode and cathode electrodes, selectively permeable membrane and electrolyte) and a cooperating connector unit with its contact structures and thermally isolated temperature sensor provides accurate measurement of the gas being analyzed together with temperature monitoring at the reaction site in a reliable and easy to use system.

Other features and advantages of the invention will be seen as the following description of a particular embodiment progresses, in conjunction with the drawings, in which:

FIG. 2 is a sectional view of the connector unit of the electrode system shown in FIG. 1;

FIG. 3 is a bottom view of the connector unit shown in FIG. 2;

FIG. 4 is a sectional view (on a larger scale) of the tip portion of the stem of the connector unit shown in FIG. 2;

FIG. 5 is a top view of the electrode subassembly of the cartridge unit of FIG. 1;

FIG. 6 is a sectional view, taken along the line 6—6 of FIG. 5 of the electrode subassembly;

FIG. 7 is a sectional view of the housing subassembly of the cartridge unit of FIG. 1.

DESCRIPTION OF PARTICULAR EMBODIMENT

Figure 1:
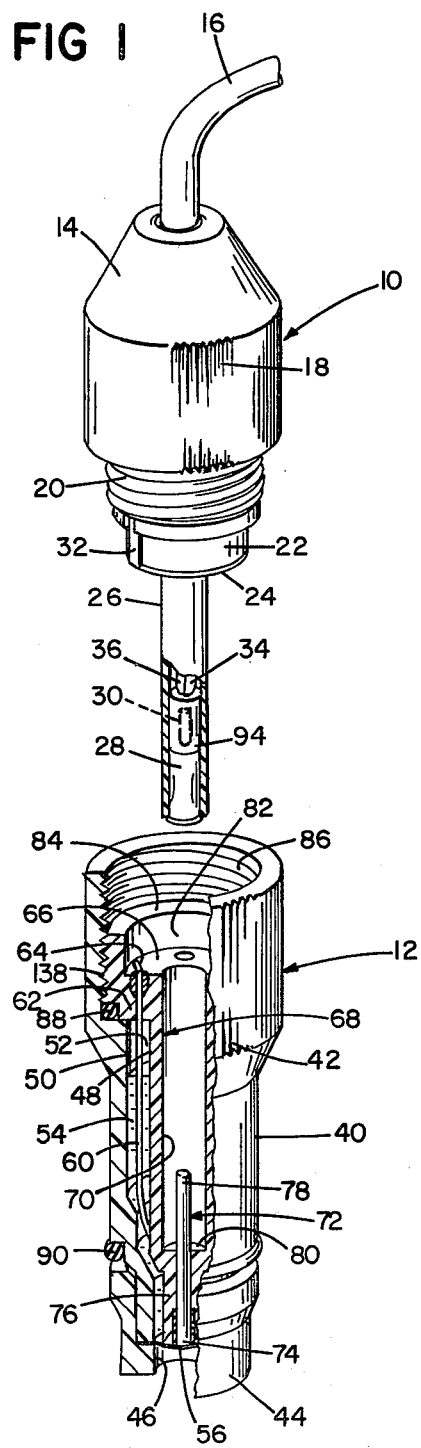
FIG. 1 is a view, with portions broken away, of connector and cartridge units of an electrode system in accordance with the invention.

The electrochemical electrode assembly shown in FIG. 1 includes a connector unit 10 and a detachable cartridge unit 12. Connector unit 10 includes a molded plastic body portion 14 that is about two centimeters in diameter and from which extends an electrical cord 16 for connection to an electrical metering device (not shown) for monitoring a particular gas concentration, such as in an anesthesia or respiratory therapy circuit. Below textured surface 18 of body 14 is a threaded coupling section 20, a cylindrical boss 22, a contact disc 24, and a tubular stem 26 of molded plastic (ABS) (of about 4.7 millimeters outer diameter, about 2.5 millimeters inner diameter, and 2.75 centimeters length) that houses at its lower end a resilient connector socket 28 and a temperature sensing thermistor 30. Contact disc 24 has opposed legs 32, one of which is connected to conductor 110 in cord 16, and conductors 34, 36 extend through stem 26 from socket 28 and sensor 30 and are similarly connected to conductors 106, 108 in cord 16.

Cartridge unit 12 has a length of about five centimeters, and includes a body member 40 that has at one end a textured surface 42 of about two centimeters diameter and at its other end an end cap 44 of about 1¼ centimeters diameter that defines a port 46 about ½ centimeter in diameter for exposure to the particular gas concentration to be monitored. Cylindrical surfaces 48, 50 of cartridge unit 12 define an annular chamber 52 that is about ⅓ filled with a potassium chloride electrolyte 54. Membrane 56 is sealed across a port at the lower end of the annular chamber 52 so that it is exposed to gas sensing port 46 of end cap 44. Silver anode electrode wire 60 is disposed in chamber 52 and extends through upper chamber wall 62 and its end forms a contact 64 on annular surface 66 in the head of insert assembly 68. Cylindrical cavity 70 that has a length of about three centimeters and a diameter of about 4.9 millimeters extends coaxially downwardly from surface 66. Projecting coaxially upward from the base of cavity 70 is silver cathode wire 72 that has its lower end surface 74 exposed to the electrolyte at the base of the tip portion 76 of the insert assembly 68. The upstanding portion 78 of cathode wire 72 projects about one centimeter from the base 80 of cylindrical cavity 70. Cartridge unit 12 has at its top end a cylindrical wall surface 82, a second annular seat surface 84 and an internal threaded section 86. O-ring 88 housed within cartridge unit 12 seals electrolyte chamber 52 and O-ring 90 is carried on the outer surface of unit 12 for sealing cooperation with a manifold or other receiving structure with which the electrode assembly is used.

Further details of connector unit 10 may be seen with reference to FIGS. 2-4. As shown in FIGS. 2 and 4, spring connector socket 28 is seated in the end of tubular stem 26. Soldered to the upper end of socket 28 is a single turn 92 of conductor 34. Seated against turn 92 is thermistor 30 that is embedded in thermal epoxy 94 such that a compact and intimate thermal assembly of socket 28 and sensor 30 is provided. One thermistor lead 36 extends upwardly through the thermal insulation air cavity 96 that is defined by stem 26 and the other thermistor lead 97 is wound around conductor 34 (as indicated in 98) and soldered to that conductor. Electrical insulation sleeve 100 overlies the soldered connection 96 and extends along the length of conductor 34 as it passes through the thermal insulation air cavity 96.

Conductors 34, 36 are attached to posts 102, 104 that are upstanding from boss 22, which posts in turn are attached to conductors 106, 108 of cable 16. A third conductor 110 is soldered to one leg 32 of contact disc 24—a disc of nickel plated hard brass that has a diameter of about one centimeter and thickness of about ½ millimeter that is seated on boss 22 of the stem member. The lower end of body member 14 is seated on flange 112 of the boss 22 and the cavity between those two members is filled with expoxy resin 114 to seal the upper end of the thermal insulation cavity 96. Axial strain relief is provided by plastic cable strip 116 that is tightened around cord 16, thus compressing it slightly, prior to the cavity being filled with resin 114. Radial strain relief is provided by the radiused opening surfaces 118 in body 14, which tend to minimize radial strain and to convert applied radial strain to axial strain which is transmitted to the axial strain relief strip 116.

The cartridge unit is composed of an insert electrode subassembly 68 shown in FIGS. 5 and 6 and a housing subassembly 120 shown in FIG. 7. Electrode subassembly 68 includes a molded polyvinylchloride member that has a head portion 122, a body portion 124 that defines guide channel 70 and tip portion 76. Silver cathode wire 72 is secured in tip portion 76 by epoxy 126 with its end surface 74 exposed at the end surface 128 of tip 76, surface 128 being coned and tapering at an angle of about seven degrees and having sufficient surface roughness to provide electrolyte flow passages. Epoxy 126 provides a gas tight seal which prevents air in guide channel 70 from reaching cathode end surface 74.

The head portion 122 has a cylindrical cavity that is defined by surfaces 66 and 82 and that defines the coaxial entrance end of elongated guide channel 70. Silver anode wire 60 passes through a first hole in head 122 and is secured with sealant 130 and its upper end 64 is bent over and seated on surface 66 to form a contact surface 64. A vent hole 132 passes through the head 122 and two blind holes 134, 136 are adapted to receive a spanner for threadedly inserting the electrode subassembly 68 into the housing subassembly 120.

Housing subassembly 120, as shown in FIG. 7, includes housing member 40 molded of polyvinylchloride, cap member 44, bilayer selectively permeable membrane 56, and O-rings 88, 90. The upper portion of housing 40 has an internal thread 86 at the base of which is seated O-ring 88. The through passage has a stepped wall surface that extends to port 140 against which membrane 56 is sealed by cap 44 that is pressfitted and secured with a solvent seal on the lower end of housing 40.

Figure 8:
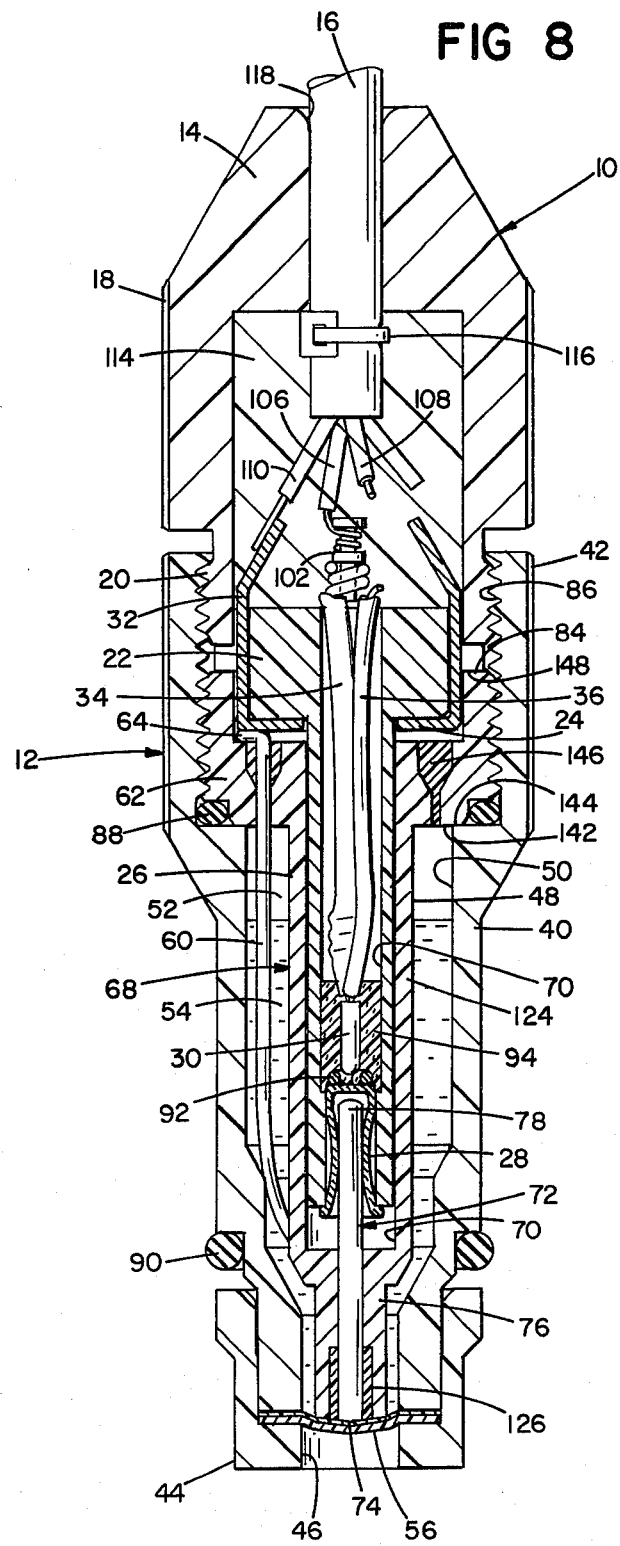
FIG. 8 is a sectional view of the assembled cartridge and connector units of the electrode system shown in FIG. 1.

The housing subassembly 120 thus is effectively an open top container into which is placed about one cubic centimeter volume of gel electrolyte 54. Electrode subassembly 68 is then inserted into housing subassembly 120, the threads 138 of head 122 being screwed down until surface 142 seats on surface 144, compressing O-ring 88 and sealing electrolyte chamber 52 as indicated in FIG. 8. When the electrode assembly 68 is seated on housing surface 144, the vent hole 132 is closed with sealant 146 as indicated in FIG. 8. In this position, the end surface 128 of the electrode subassembly 68 projects about ¼ millimeter beyond the end surface of housing 40 (at port 140) so that membrane 56 is flexed and tensioned into the desired cathode-membrane-electrolyte interface configuration. The roughened end surface 128 provides minute electrolyte flow passages for maintaining electrical continuity between cathode 72 and anode 60.

In use, detachable cartridge unit 12 is attached to connector unit 10 simply by inserting stem 26 into stem guide channel 70 where it is guided along the side walls to initial piloting interengagement of cathode wire 72 with connector socket 28. When the threads 20 and 86 become engaged, the connector unit 10 and cartridge unit 12 are then threaded together, the helical interengagement motion of connector socket 28 and cathode wire 72 involving a wiping action that makes a reliable electrical connection made between cathode 72 and conductor 106 via connector socket 28, while the contact tip 64 of anode electrode 60 is concurrently being compressed and distorted by the helical sliding engagement of contact plate 24 to provide a reliable electrical connection between anode 60 and conductor 110, with boss surface 148 (FIG. 2) finallly being seated on connector unit surface 84 (FIG. 6). The cylindrical air gap between stem 26 and cartridge cavity 70 provides thermal isolation.

In this assembled position as shown in FIG. 8, the electrode assembly is ready for insertion into a test manifold for monitoring the gas of interest. Cartridge 12 provides an easily replaced, modular assembly with a premounted selectively permeable membrane-electrode array in an easy to assemble structure in which the electrolyte is sealed, and which facilitates maintenance as needed, for example, due to electrolyte depletion as well as the selection of different electrode subassemblies for measurements of other gases. The thermally isolated temperature sensor-connector socket assembly of the connector unit provides accurate monitoring of reaction site temperature at the membrane-cathode interface in the cartridge unit.

While a particular embodiment of the invention has been shown and described, various modifications will be apparent to those skilled in the art, and therefore it is not intended that the invention be limited to the discolsed embodiment or to details thereof, and departures may be made therefrom within the spirit and scope of the invention.

What is claimed is:

1. A replaceable cartridge assembly for use with electrochemical analysis apparatus comprising housing structure of electrically insulating material that defines an annular electrolyte chamber, coupling structure at one end of said housing structure, an electrolyte chamber port at the other end of said housing structure, a selectively permeable membrane extending across said port in sealing relation thereto, an elongated cavity within said housing structure that has an open port adjacent said coupling structure through which the projecting stem of a cooperating connector component is adapted to be inserted, said cavity being bounded by an end wall remote from said coupling structure and by side wall structure of electrically insulating material extending between said port and said end wall that defines the inner wall of said annular electrolyte chamber, a cathode electrode extending through said cavity end wall with a cathode electrode contact surface exposed at the base of said cavity for engagement with an electrical contact member carried at the end of said projecting stem, said cathode electrode having a tip at its end opposite said cathode electrode contact surface in juxtaposed relation to said membrane, an anode electrode extending through a wall of said housing with an anode electrode contact surface exposed adjacent said coupling structure and a major portion of said anode electrode disposed in said electrolyte chamber, and electrolyte in said annular chamber such that said electrolyte is disposed annularly around said cathode electrode and extends through said port into the region between said membrane and the tip of said cathode electrode to provide an electrically conductive path between said anode and cathode electrodes.

2. The assembly of claim 1 wherein said housing structure includes a tubular housing of electrically insulating material that defines a through passage, said coupling structure being at one end of said tubular housing and said electrolyte chamber port being at the other end of said tubular housing, and an insert subassembly that is secured in said tubular housing, said subassembly including flange structure at one end for coupling to said tubular housing through passage and a stem portion of electrically insulating material extending axially from said flange structure, said stem portion defining said elongated cavity and said electrolyte chamber being defined between said stem portion and said tubular housing.

3. the assembly of claim 2 wherein said flange structure has a planar surface and said anode electrode is a metal wire and an end of said anode electrode wire projects above said planar surface of said flange structure and defines said anode contact surface.

4. The assembly of claim 3 wherein said cathode and anode electrodes are silver wires.

5. The assembly of claim 2 wherein said coupling structure is of the screw-type and said flange structure of said insert subassembly is coupled to said tubular housing by means of said screw-type coupling structure.

6. The assembly of claim 1 wherein said elongated cavity is of cylindrical configuration and has a length to diameter ratio of at least four, said coupling structure is of the screw type, said housing includes an annular surface that is recessed below said screw type coupling structure, said planar surface defining said cavity port and extending radially thereabout, said anode electrode has a portion that projects through and above said annular surface that defines said anode contact surface, and said cathode electrode has a portion that extends coaxially upwardly from the end wall of said cylindrical cavity and defines said cathode electrode contact surface.

7. A replaceable cartridge assembly for use with electrochemical analysis apparatus comprising housing structure of electrically insulating material that defines an annular electrolyte chamber, coupling structure at one end of said housing structure, an electrolyte chamber port at the other end of said housing structure, a selectively permeable membrane extending across said port in sealing relation thereto, an elongated cavity within said housing structure that has an open port adjacent said coupling structure through which the projecting stem of a cooperating connector component is adapted to be inserted, said cavity being bounded by an end wall remote from said coupling structure and by side wall structure extending between said port and said end wall that defines the inner wall of said annular electrolyte chamber, a cathode electrode extending through said cavity end wall with a cathode electrode contact surface exposed at the base of said cavity for engagement with an electrical contact member carried at the end of said projecting stem, said cathode electrode contact structure being in the form of a coaxially projecting length of said cathode electrode that extends upwardly from said cavity end wall and said cathode electrode having a tip at its end opposite said cathode electrode contact surface in juxtaposed relation to said membrane, an anode electrode extending through a wall of said housing with an anode electrode contact surface exposed adjacent said coupling structure and a major portion of said anode electrode disposed in said electrolyte chamber, and electrolyte in said annular chamber such that said electrolyte is disposed annularly around said cathode electrode and extends through said port into the region between said membrane and the tip of said cathode electrode to provide an electrically conductive path between said anode and cathode electrodes.

8. A connector assembly for use with a replaceable cartridge unit in an electrochemical electrode apparatus, said cartridge unit including coupling structure, structure defining an electrolyte chamber, a port at one end of said electrolyte chamber, a selectively permeable membrane extending across said port in sealing relation thereto, structure defining a recess within said cartridge unit, a cathode electrode supported in said recess with the tip of said cathode electrode in juxtaposed relation to said membrane and a cathode electrode contact surface in said recess, an anode electrode with an anode electrode contact surface exposed adjacent said coupling structure and a major portion of said anode electrode disposed in said electrolyte chamber, and electrolyte in said chamber such that said electrolyte extends through said port into the region between said membrane and the tip of said cathode electrode to provide an electrically conductive path between said anode and cathode electrodes;

said connector assembly including a fixed projecting stem of electrically insulating material, a first electrical contact member at the end of said stem for electrically engaging said cathode electrode contact surface, an electrical conductor extending through said stem from said first contact member, a temperature sensor in said stem in intimate thermal association with said first contact member, a second electrical contact member at the end of said stem remote from said first contact member for electrically engaging said anode electrode contact surface, coupling structure for engagement with said coupling structure of said cartridge unit to interconnect said cartridge unit and said connector assembly with said second contact member in electrical engagement with said anode contact and said first contact member in electrical engagement with said cathode contact; and means for electrically connecting said contact members to a remote location to conduct the electrical signal provided by said electrodes to said remote location.

9. The assembly of claim 8 wherein first electrical contact member and said temperature sensor are embedded in thermally conductive material at the end of said stem.

10. The assembly of claim 8 wherein said projecting stem is of cylindrical configuration and has a length to diameter ratio of at least four, said first electrical contact member is of the resilient socket type with an opening coaxially disposed at the end of said stem, said second electrical contact member is an annular contact that surrounds said stem at the end of said stem adjacent said coupling structure, and said coupling structure is of the screw type.

11. The assembly of claim 8 wherein thermal insulation is provided in said projecting stem between said temperature sensor and said coupling structure.

12. The assembly of claim 11 wherein said thermal insulation is a sealed air gap region.

13. The assembly of claim 12 wherein said first electrical contact member is of the resilient socket type, said temperature sensor has a first lead extending through said stem and a second lead electrically connected to said conductor; and said second electrical contact member is an annular contact that surrounds said stem at the end remote from said socket.

14. An electrochemical electrode assembly comprising a detachable cartridge component and a cooperating connector component, said cartridge component comprising housing structure of electrically insulating material that defines an annular electrolyte chamber, coupling structure at one end of said housing, an electrolyte chamber port at the other end of said housing, a selectively permeable membrane extending across said port in sealing relation thereto, an elongated cylindrical cavity within said housing bounded by an end wall remote from said coupling structure and by wall structure of electrically insulating material that defines the inner wall of said annular electrolyte chamber, a cathode electrode extending through said cavity end wall with the tip of said coaxially projecting length of said cathode electrode in juxtaposed relation to said membrane and a coaxially projecting length of said cathode electrode in said elongated cavity, an anode electrode extending through a wall of said housing with an anode electrode contact surface exposed adjacent said coupling structure and a portion of said anode electrode disposed in said electrolyte chamber, and electrolyte in said annular chamber such that said electrolyte is disposed annularly around said cathode electrode and extends through said port into the region between said membrane and the tip of said cathode electrode to provide an electrically conductive path between said anode and cathode electrodes;

said connector component including a fixed projecting cylindrical stem of electrically insulating material, a first electrical contact member at the end of said stem for electrically engaging said coaxially projecting length of said cathode electrode, an electrical conductor extending through said stem from said contact structure, a temperature sensor in said stem in intimate thermal association with said first contact member, a second electrical contact member at the end of said stem remote from said first contact member for electrically engaging said anode electrode contact surface, and coupling structure for engagement with said coupling structure of said cartridge component to interconnect said cartridge component and said connector component with said stem disposed in said elongated cavity so that an annular air gap is provided therebetween, said second contact member is in electrical engagement with said anode contact and said first contact member is in electrical engagement with said cathode contact; and means for electrically connecting said electrode assembly to a remote location to conduct the electrical signal provided by said electrode assembly to said remote location.

15. An electrochemical electrode assembly comprising a detachable cartridge component and a cooperating connector component, said cartridge component comprising housing structure of electrically insulating material that defines an annular electrolyte chamber, coupling structure at one end of said housing, an electrolyte chamber port at the other end of said housing, a selectively permeable membrane extending across said port in sealing relation thereto, an elongated cavity within said housing bounded by an end wall remote from said coupling structure and by wall structure that defines the inner wall of said annular electrolyte chamber, a cathode electrode wire extending through said cavity end wall with the tip of said cathode electrode wire in juxtaposed relation to said membrane and a coaxially projecting length of said cathode wire extending upwardly from said cavity end wall to provide a cathode electrode contact surface in said elongated cavity, an anode electrode extending through a wall of said housing with an anode electrode contact surface exposed adjacent said coupling structure and a portion of said anode electrode disposed in said electrolyte chamber, and electrolyte in said annular chamber such that said electrolyte is disposed annularly around said cathode electrode and extends through said port into the region between said membrane and the tip of said cathode electrode wire to provide an electrically conductive path between said anode an cathode electrodes;

said connector component incuding a projecting stem, a first electrical contact member at the end of said stem for electrically engaging said cathode electrode contact surface, an electrical conductor extending through said stem from said first contact member, a temperature sensor in said stem in intimate thermal association with said first contact member, a second electrical contact member at the end of said stem remote from said first contact member for electrically engaging said anode electrode contact surface, and coupling structure for engagement with said coupling structure of said cartridge component to interconnect said cartridge component and said connector component with said stem disposed in said elongated cavity so that an annular air gap is provided therebetween, said second contact member is in electrical engagement with said anode contact and said first contact member is in electrical engagement with said cathode contact; and means for electrically connecting said electrode assembly to a remote location to conduct the electrical signal provided by said electrode assembly to said remote location.

16. An electrochemical electrode assembly comprising a detachable cartridge component and a cooperating connector component, said cartridge component comprising housing structure of electrically insulating material that defines an annular electrolyte chamber, coupling structure at one end of said housing, an electrolyte chamber port at the other end of said housing, a selectively permeable membrane extending across said port in sealing relation thereto, an elongated cylindrical cavity within said housing bounded by an end wall remote from said coupling structure and by wall structure that defines the inner wall of said annular electrolyte chamber, said cavity having a length to diameter ratio of at least four, a cathode electrode extending through said cavity end wall with the tip of said cathode electrode in juxtaposed relation to said membrane and a cathode electrode contact surface in said elongated cavity, an anode electrode extending through a wall of said housing with an anode electrode contact surface exposed adjacent said coupling structure and a portion of said anode electrode disposed in said electrolyte chamber, and electrolyte in said annular chamber such that said electrolyte is disposed annularly around said cathode electrode and extends through said port into the region between said membrane and the tip of said cathode electrode to provide an electrically conductive path between said anode and cathode electrodes;

said connector component including a projecting cylindrical stem, said stem having a length to diameter ratio of at least four, a first electrical contact member at the end of said stem for electrically engaging said cathode electrode contact surface, an electrical conductor extending through said stem from said first contact member, a temperature sensor in said stem in intimate thermal association with said first contact member, a second electrical contact member at the end of said stem remote from said first contact member for electrically engaging said anode electrode contact surface, and coupling structure for engagement with said coupling structure of said cartridge component to interconnect said cartridge component and said connector component with said stem disposed in said elongated cavity so that an annular air gap is provided therebetween, said second contact member is in electrical engagement with said anode contact and said first contact member is in electrical engagement with said cathode contact; and means for electrically connecting said electrode assembly to a remote location to conduct the electrical signal provided by said electrode assembly to said remote location.

17. The assembly of claim 16 wherein first electrical contact member is of the resilient socket type, said temperature sensor has a first lead extending through said stem and a second lead electrically connected to said conductor; and said second electrical contact member is an annular contact that surrounds said stem at the end remote from said socket.

18. The assembly of claim 17 wherein said housing structure incudes a tubular housing of electrically insulating material that defines a through passage, said coupling structure being at one end of said tubular housing and said electrolyte chamber port being at the other end of said tubular housing, and an insert subassembly secured in said tubular housing, said subassembly including flange structure at one end sealingly attached to said tubular housing through passage and a tubular stem portion of electrically insulating material extending axially from said flange structure, said tubular stem portion defining said elongated cavity and said electrolyte chamber being defined between said stem portion and said tubular housing.

19. The assembly of claim 18 wherein said cathode electrode is a metal wire and said cathode electrode contact surface is a coaxially projecting length of said cathode wire that extends upwardly from said cavity end wall, said flange has a planar surface and said anode electrode is a metal wire and an end of said anode electrode wire projects above said planar surface of said flange structure and defines said anode contact surface.

20. The assembly of claim 19 wherein said coupling structure is of the screw-type and said resilient socket wipingly engages said coaxially upwardly projecting cathode wire and said annular contact wipingly engages said anode wire to complete electrical circuits when the threads of the screw type coupling structures are engaged and helically threaded together.

* * * * *